ns Patent [19]

Fujiwhara et al.

[11] 4,057,432
[45] Nov. 8, 1977

[54] ACYLACETANILIDE COUPLER WITH HETEROCYCLIC DIACYL AMINO COUPLING-OFF GROUP

[75] Inventors: Mitsuto Fujiwhara, Hachioji; Tamotsu Kojima, Kokubunji; Syunji Matsuo, Fussa, all of Japan

[73] Assignee: Konishiroku Photo Industry Co., Ltd., Tokyo, Japan

[21] Appl. No.: 379,730

[22] Filed: July 16, 1973

Related U.S. Application Data

[63] Continuation of Ser. No. 211,468, Dec. 23, 1971, abandoned.

[30] Foreign Application Priority Data

Dec. 26, 1970 Japan .................. 45-119053

[51] Int. Cl.² .......................... G03C 7/00; G03C 1/40
[52] U.S. Cl. .................... 96/56.2; 96/100 N
[58] Field of Search ............ 96/100, 56.2, 55

[56] References Cited

U.S. PATENT DOCUMENTS

| | | | |
|---|---|---|---|
| 2,992,920 | 7/1961 | De Cat et al. | 96/56.2 |
| 3,458,315 | 7/1969 | Loria | 96/56.2 |
| 3,516,831 | 6/1970 | Wolf et al. | 96/100 |
| 3,730,722 | 5/1973 | Inoue et al. | 96/56.3 |

*Primary Examiner*—David Klein
*Assistant Examiner*—Richard L. Schilling
*Attorney, Agent, or Firm*—Bierman & Bierman

[57] ABSTRACT

A process for forming yellow image in a light-sensitive silver halide photographic material which uses as a yellow image-forming a coupler a compound of the formula

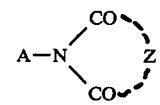

wherein A is a yellow image-forming coupler residue having an active methylene group;

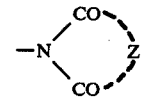

is a group which has been substituted for one hydrogen atom of the active methylene group in said coupler residue A; and Z is a group selected from alkylene, alkenylene, cycloalkylene, cycloalkenylene, terphenylene, arylene and pyridine-diyl groups.

6 Claims, 1 Drawing Figure

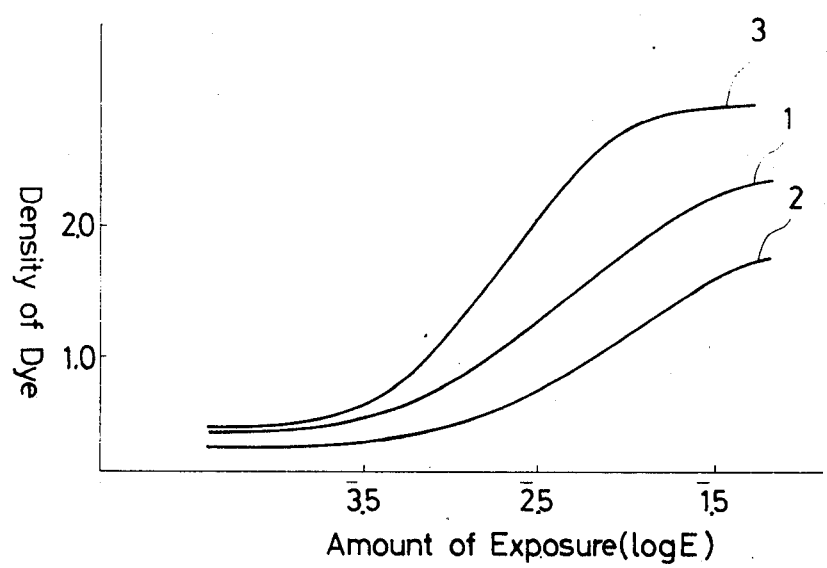

ACYLACETANILIDE COUPLER WITH HETEROCYCLIC DIACYL AMINO COUPLING-OFF GROUP

This application is a Rule 60 continuation of application Ser. No. 211,468, filed Dec. 23, 1971, now abandoned; which in turn claims the priority of Japanese application No. 119,053/70 filed Dec. 26, 1970.

This invention relates to a process for forming a yellow image in a light-sensitive color photographic material. More particularly, the invention pertains to a process for forming a yellow dye image in a light-sensitive color photographic material by use of a novel yellow dye image-forming 2-equivalent coupler.

A photographic process for forming a dye image by exposing a photographic material containing couplers and then color-developing the exposed photographic material with a developer containing an aromatic primary amine type developing agent has been known for sometime. Of the couplers used in the above-mentioned process, the yellow coupler has an active methylene group which serves to form a dye by coupling with an oxidation product of the aromatic primary amine type developing agent. In case this active methylene group has no substituent, four molecules of silver halide are required in order to form one molecule of the dye by color development. That is, a so-called 4-equivalent coupler is required. However, it is well known that the same dye as in the case of the 4-equivalent coupler can be formed also from a coupler having a methylene group in which one of the hydrogen atoms has been substituted by a halogen atom such as chlorine. In this case, the halogen atom is released during the color development reaction, and one molecule of a dye is formed from two molecules of the developed silver halide. Accordingly, the said coupler is called a 2-equivalent coupler.

The 2-equivalent coupler is more advantageous than the known 4-equivalent coupler in the following points:

1. The coupling rate becomes higher than in the case of the 4-equivalent coupler.
2. The amount of silver halide required to obtain a definite amount of dye may be one half the amount required in the case of the 4-equivalent coupler, so that the production cost of light-sensitive material can be reduced.
3. The emulsion layer can be made thinner, and thus the resulting color image is increased in resolution and sharpness.
4. In the case of a multi-layered light sensitive material, the transmission of light into the lower layers is enhanced, and thus the photographic speed of the light-sensitive material is improved.

In view of the above, the use of the 2-equivalent coupler brings about great advantages in forming a color image in a multi-layered light-sensitive color photographic material. These advantages are particularly marked when one of the hydrogen atoms of the active methylene group of a yellow image-forming coupler has been substituted by a cyclic acid imide such as

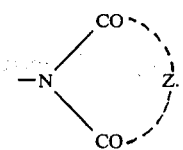

This substituent has the property of being releasable at the time of color development.

Certain 2-equivalent couplers tend to form color stains or to disturb the development. However, the 2-equivalent coupler used in the present invention is not only colorless but also highly reactive, and hence forms scarcely any color stains. Further, a yellow dye formed by the aforesaid color development from the yellow coupler used in the present invention is excellent in fastness to light, humidity and heat, has no unnecessary absorption in the long wavelength portion, is less in absorption at the green light region, shows a sharp absorption, and has hues which are quite desirable for color reproduction.

The 2-equivalent coupler used in the present invention has the following general formula:

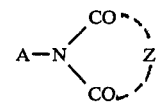

wherein A is a yellow image-forming coupler residue having a methylene group;

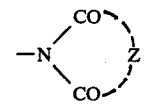

is a group which has been substituted for one hydrogen atom of the active methylene group of said coupler residue A; and Z is a group selected from alkylene, alkenylene, cycloalkylene, cycloalkenylene, terphenylene, arylene and pyridine-diyl groups.

Typical examples of the substituent for an active methylene group of the coupler used in the present invention are shown below.

2,2-Dipropyl-malonimide
Succinimide
2-Methylsuccinimide
2-Tetradecylsuccinimide
2-Cyclohexylsuccinimide
2-(p-Nitrophenyl)succinimide
2-(p-Chlorophenyl)-3-methylsuccinimide
2-Hydroxysuccinimide
2-Methoxysuccinimide
2-Benzyl-2-acetylsuccinimide
2-Carbamoylsuccinimide
2-Aminosuccinimide
2-Acetamidosuccinimide
2-Cyano-2-benzylsuccinimide
2-Methylenesuccinimide
2-Chlorosuccinimide
Maleimide
2-Methylmaleimide
2-Methyl-3-dodecylmaleimide
2-(p-Methoxyphenyl)maleimide
2,3-Dicyanomaleimide
2-Methoxy-3-cyanomaleimide
2-Methoxymaleimide
2-Anilinomaleimide
2-Trifluoromethylmaleimide
1,2-Cyclohexanedicarboximide
4-Phenyl-1,2-cyclohexanedicarboximide
3,6-Epoxy-1,2-cyclohexanedicarboximide
3-Cyclohexene-1,2-dicarboximide
4-Cyclohexene-1,2-dicarboximide 5-Norbornel-2,3-dicarboximide
Phthalimide
4,5-Dimethylphthalimide
4-Phenylphthalimide
4-Aminophthalimide
4-Laurylamidophthalimide
4-Methoxyphthalimide
3-Nitrophthalimide
4-Nitrophthalimide
4-Chlorophthalimide
3,4,5,6-Tetrafluorophthalimide
4,5-Dicyanophthalimide
4-Sulfamoylphthalimide
4-Benzoylphthalimide
4-Acetylphthalimide
4-Trifluoromethylphthalimide
4,4′-Carbonyldiphthalimide
Benzene-1,2,4,5-tetracarboxydiimide
1,2-Naphthalenedicarboximide
2,3-Naphthalenedicarboximide
2,3-Pyridinedicarboximide
3,4-Pyridinedicarboximide Typical examples of the couplers used in the present invention are shown below, but couplers usable in the present invention are not limited to these. Exemplified couplers α-Succinimido-α-pivalyl-2-chloro-5-[γ-(2,4-di-t-amylphenoxy)butylamide]acetanilide (1)

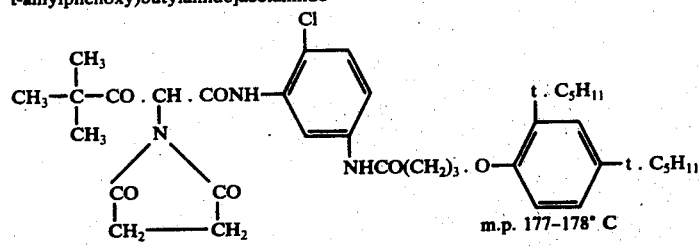

m.p. 177–178° C

α-Succinimido-α-benzoyl-2-methoxyacetanilide (2)

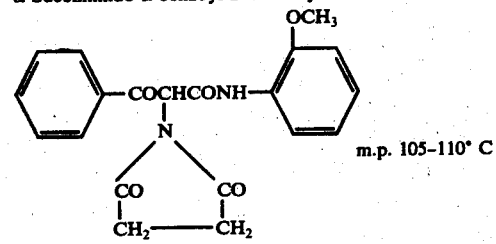

m.p. 105–110° C

α-(2-Tetradecylsuccinimido)-α-pivalylacetanilide (3)

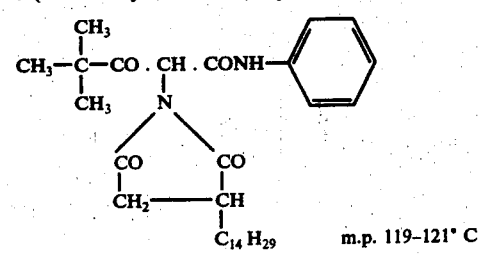

m.p. 119–121° C

Sodium α-(2-methoxysuccinimido)-α-(p-dodecyloxybenzoyl)-3,5-dicarboxyacetanilide (4)

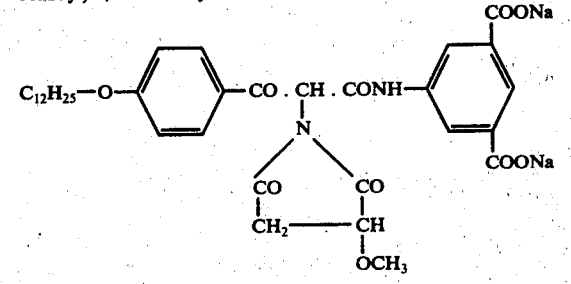

decomp.p. Above 250° C

α-(Cyclohexane-1,2-dicarboximido)-α-pivalylacetanilide (5)

-continued
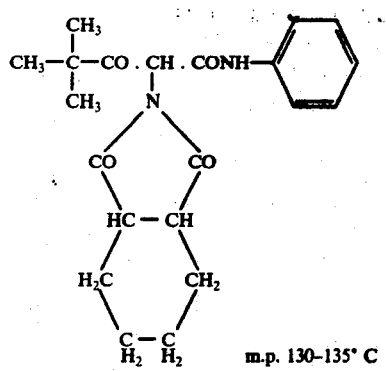
m.p. 130–135° C
α-(5-Norbornene-2,3-dicarboximido)-α-pivalylacetanilide (6)
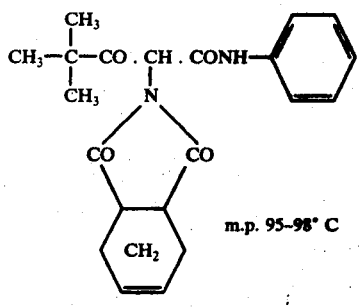
m.p. 95–98° C
α-Phthalimide-α-pivalyl-2-chloro-5-[γ-(2,4-di-t-amylphenoxy)butylamido]acetanilide (7)
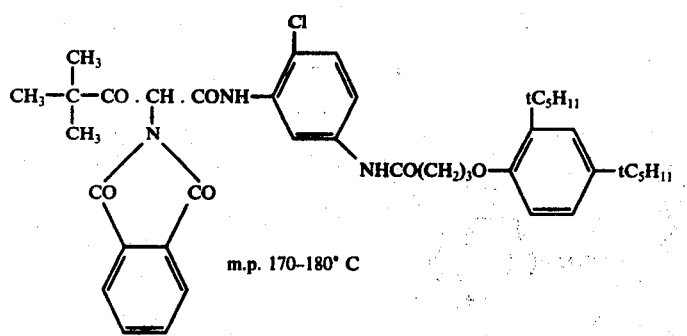
m.p. 170–180° C
α-Phthalimide-α-benzoyl-2-chloro-5-[γ-(2,4-di-t-amylphenoxy)butylamido]acetanilide (8)
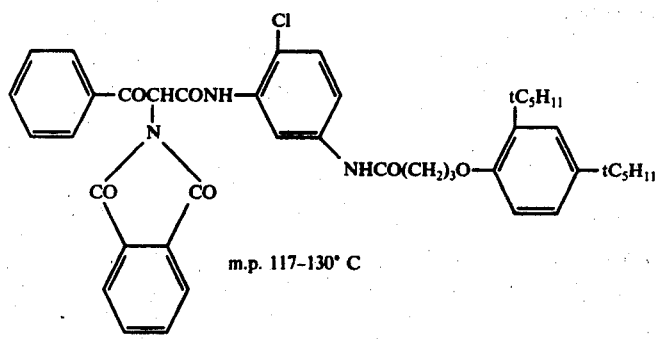
m.p. 117–130° C
α-(4-Nitrophthalimido)-α-pivalylacetanilide (9)

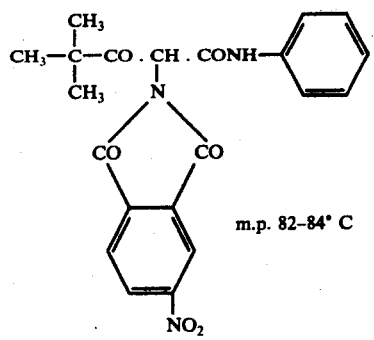
m.p. 82–84° C
Potassium α-(2,3-pyridinedicarboximido)-α-furoyl-3,5-dicarboxyacetanilide   (10)
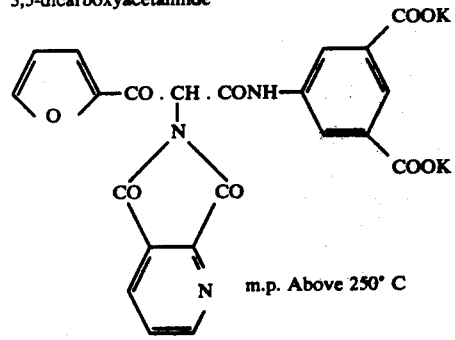
m.p. Above 250° C
α-Maleimide-α-pivalylacetanilide   (11)
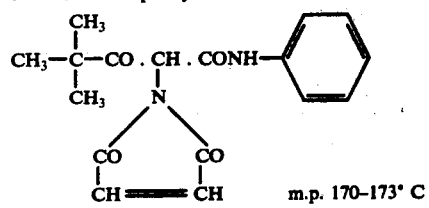
m.p. 170–173° C
α-{3-[α-(2,4-Di-t-amylphenoxy)butylamido]benzoyl}-α-succinimido-2-methoxyacetanilide   (12)
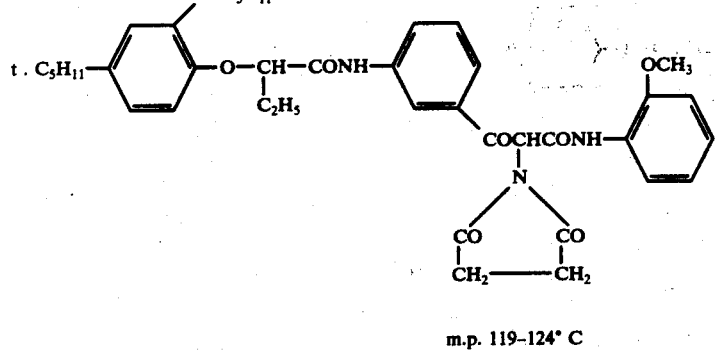
m.p. 119–124° C
α-(2-Methylsuccinimido)-α-benzoyl-5-[α-(n-dodecyloxycarbonyl)ethoxycarbonyl]-2-chloroacetanilide   (13)
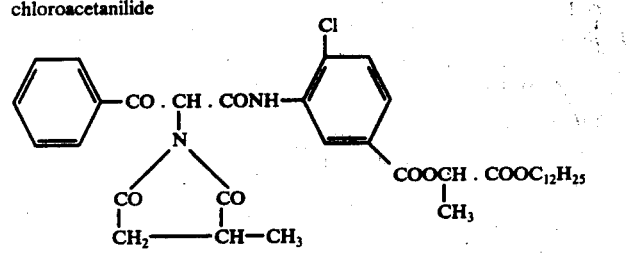
m.p. 78–79° C -continued α-(2,2-Dipropylmalonimido)-α-pivalylacetanilide (14)

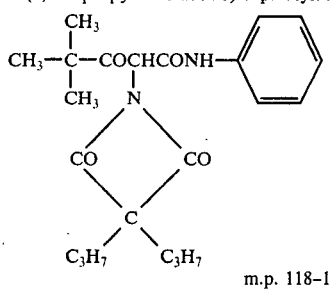

m.p. 118–120° C

The above-mentioned compounds can be synthesized, for example, by reacting a yellow image-forming coupler having an active methylene group, in which one of the hydrogen atoms of the active methylene group has been substituted by a halogen atom, with a diacylimide in an inert solvent.

Procedures for synthesis of the couplers used in the present invention are set forth below with reference to synthesis examples, but the invention is not limited to these.

Synthesis Example 1

Synthesis of the exemplified coupler (1)

A mixture comprising 13 g. of α-pivalyl-α-bromo-2-chloro-5-[γ-(2,4-di-t-amylphenoxy)butylamido] acetanilide, 2 g. of succinimide and 3 g. of triethylamine was heated under reflux for 12 hours in 100 ml. of acetonitrile. Thereafter, the liquid reaction mixture was vaporized to dryness under reduced pressure, and the residue was recrystallized from a mixed solvent comprising hexane and alcohol to obtain 7 g. of white powdery crystals, m.p. 175°–178° C.

Elementary analysis:

|  | C | H | N |
|---|---|---|---|
| Calculated (%) | 66.50 | 7.54 | 6.29 |
| Found (%) | 66.50 | 7.46 | 6.13 |

Synthesis Example 2

Synthesis of the exemplified coupler (2)

A mixture comprising 17.0 g. of α-chloro-α-benzoyl-2-methoxyacetanilide and 9.5 g. of potassium salt of succinimide was heated under reflux for 2 hours in 150 ml. of acetonitrile. Thereafter, the liquid reaction mixture was filtered and the filtrate was vaporized to dryness under reduced pressure. Subsequently, the residue was recrystallized from a mixed solvent comprising n-hexane and alcohol to obtain 10 g. of white powdery crystals, m.p. 105°–110° C.

Elementary analysis:

|  | C | U | N |
|---|---|---|---|
| Calculated (%) | 65.56 | 4.95 | 7.65 |
| Found (%) | 65.61 | 5.05 | 7.53 |

Synthesis Example 3

Synthesis of the exemplified coupler (8)

A mixture comprising 6.7 g. of α-bromo-α-benzoyl-2-chloro-5-[γ-(2,4-di-t-amylphenoxy)butylamido]acetanilide and 2.8 g. of potassium salt of phthalimide was heated under reflux for 1 hour in 100 ml. of acetonitrile. Thereafter, the liquid reaction mixture was filtered, and the filtrate was vaporized to dryness. Subsequently, the residue was recrystallized from a mixed solvent comprising n-hexane and alcohol to obtain 3 g. of white powdery crystals, m.p. 117°–130° C.

Elementary analysis:

|  | C | H | N |
|---|---|---|---|
| Calculated (%) | 70.14 | 6.30 | 5.71 |
| Found (%) | 70.25 | 6.21 | 5.74 |

Developing agents for use in the development adopted in the process of the present invention are the following aromatic primary amine type developing agents:

Diethyl-p-phenylenediamine hydrochloride
Monomethyl-p-phenylenediamine hydrochloride
Dimethyl-p-phenylenediamine hydrochloride
2-Amino-5-diethylaminotoluene hydrochloride
2-Amino-5-(N-ethyl-N-dodecylamino)-toluene
N-Ethyl-N-β-methanesulfonamidoethyl-3-methyl-4-aminoaniline hydrochloride
N-Ethyl-N-β-methanesulfonamidoethyl-4-aminoaniline
4-N-Ethyl-N-β-hydroxyethyl-aminoaniline Further, aminophenol derivatives, whose amino groups have not been substituted, can be used in alkaline developers. Certain couplers used in the present invention are incorporated into alkaline developers.

The developers used may contain sulfites, carbonates, bisulfites, bromides or iodides of alkali metals.

An example of typical developers containing the couplers used in the present invention is as follows:

| 2-Amino-5-diethylaminotoluene hydrochloride | 2.0 g. |
|---|---|
| Anhydrous sodium sulfite | 2.0 g. |
| Anhydrous sodium carbonate | 20.0 g. |
| Potassium bromide | 1.0 g. |
| Exemplified coupler (2) | 2.0 g. |
| Water to make | 1,000 ml. |

In order to incorporate the couplers used in the present invention into a light-sensitive color photographic emulsion, there may be adopted any of the known procedures. For example, the couplers are dissolved either independently or in the form of a mixture in a high boiling solvent having a boiling point of more than 175° C. such as tricresyl phosphate or dibutyl phthalate, or in a low boiling solvent such as butyl acetate or butyl propionate (or in a mixture thereof), and the resulting solution is mixed with an aqueous solution containing a surface active agent. Thereafter, the mixed solution is subjected to a high speed rotary mixer or colloid mill to form a dispersion. Subsequently, the thus formed dispersion is directly added to a silver halide photographic emulsion, which is then coated on a support and dried. Alternatively, the above-mentioned coupler dispersion is set, finely cut, freed from the low boiling solvent by water-washing or like means, and thereafter added to the photographic emulsion, which is then coated on a support and dried. In this case, the amount of the coupler incorporated is preferably 10 to 300 g. per mole of the silver halide, but may be varied depending on the application purpose.

The yellow dye image-forming 2-equivalent coupler used in the present invention, e.g. the exemplified coupler (1), (7) or (8), can be dispersed according to the above-mentioned procedure in a photographic emulsion, without using a high boiling solvent. The exemplified coupler (4) can be dispersed in a photographic emulsion according to Fisher's method. The exemplified coupler (2) may be incorporated into a developer, and the exemplified coupler (3) may be used for diffusion transfer because it forms a diffusing dye.

The photographic emulsion used in the present invention may contain any of such silver halides as silver chloride, silver iodobromide or silver chlorobromide, and may be subjected to chemical sensitization or to optical sensitization using a carbocyanine or merocyanine dye. Further, the photographic emulsion may be incorporated therein ordinary photographic additives such as antifoggants, stabilizers, anti-stain agents, anti-irradiation agents, physical property-improving high polymer additives, hardeners, coating aids, etc.

When an ultraviolet absorber is incorporated therein, a light-sensitive color photographic material containing the coupler used in the present invention can be further improved in fastness of the resulting color image. Further, the color developer used in the present invention may contain such development-controlling agents as, for example, citrazinic acid, in addition to the aforesaid developing agent.

The accompanying drawing is a graph showing the density of yellow dye to blue light at each stage described in Example 2 of the present invention. In the graph, the horizontal axis represents the amount of exposure (log E) and the vertical axis the density of dye.

The present invention is illustrated in further detail below with reference to examples, but the scope of the invention is not limited only to these examples.

EXAMPLE 1

20.0 Grams of each of the exemplified couplers (1), (7) and (8) was added to a mixed solvent comprising 20 ml. of dibutyl phthalate and 60 ml. of ethyl acetate and then heated to 60° C., whereby the coupler was completely dissolved. This solution was mixed with 10 ml. of a 6% aqueous solution of Alkanol B (alkylnaphthalenesulfonate produced by Du Pont) and 200 ml. of a 6% aqueous gelatin solution, and then subjected to a colloid mill to form a coupler dispersion. This coupler dispersion was added to 1 kg. of a high speed silver iodobromide emulsion, which was then coated on a film base and dried to prepare a light-sensitive photographic material having stable coating. The thus prepared photographic material was exposed according to an ordinary procedure and then developed at 20° C. for 10 minutes with a developer of the following composition:

| | |
|---|---|
| N-Ethyl-N-$\beta$-methanesulfonamidoethyl-3-methyl-4-aminoaniline sulfate | 5.0 g. |
| Anhydrous sodium sulfite | 2.0 g. |
| Benzyl alcohol | 3.8 g. |
| Sodium carbonate (monohydrate) | 50.0 g. |
| Potassium bromide | 1.0 g. |
| Sodium hydroxide | 0.55 g. |
| Water to make | 1,000 ml. |

Thereafter, the developed photographic material was subjected to ordinary stopping, fixing and bleaching treatments.

For comparison, photographic materials were prepared in the same manner as above, except that coupler identical in structure, except that it has a substituent-free active methylene group, was used as a control, and then subjected to the same treatment as above.

The absorption maximum ($\lambda$max), maximum density ($D$max) and storability of each of the resulting images were as set forth in Table 1.

Table 1

| Run No. | Coupler No. | $\lambda_{max}$ | $\lambda_{Dmax}$ | Color image Residual ratio Light fastness | Moisture fastness |
|---|---|---|---|---|---|
| 1 | Control | 447 | 1.74 | 96 | 100 |
| 2 | (1) | 447 | 2.68 | 97 | 100 |
| 3 | Control | 447 | 1.72 | 95 | 99 |
| 4 | (7) | 447 | 2.65 | 96 | 100 |
| 5 | Control | 452 | 2.30 | 80 | 100 |
| 6 | (8) | 453 | 2.80 | 82 | 100 |

$\lambda$,Max, Dmax: Calculated by measuring spectral absorption and density
Residual ratio: Ratio (%) of residual color after treating portions having an initial density of 1.0.
Treatment conditions:
Light fastness: Xenon arc lamp, 50° C., 30 hrs.
Moisture fastness: 50° C. 80% RH, 7 days.

As seen in Table 1, the couplers of the present invention show excellent characteristics and are usable as elements for multi-layered and multi-colored photographic materials.

EXAMPLE 2

According to the procedure described in Example 1, the exemplified coupler (1) was dispersed in a gelatin-silver iodobromide emulsion. In this case, the silver halide was used in one half the amount of that used in Example 1.

For comparison, a 4-equivalent coupler identical in structure, except that it has a substituent-free active methylene group, was used as a control and dispersed in the same emulsion as above and the amount of the silver halide used was made identical with, and one half, the amount of that used in Example 1.

These emulsions are individually treated in the same manner as in Example 1 to prepare light-sensitive photographic materials, which were then exposed and thereafter developed with the same developer as in Example 1.

The density of yellow dye to blue light at each stage was measured by means of a densitometer and shown in the accompanying drawing, in which the horizontal axis shows the amount of exposure (log E) and the vertical axis the density. The curves 1 and 2 show the case of the photographic materials containing the 4-equivalent coupler, and the curve 3 shows the case of the photographic material containing the coupler used in the present invention. The amount of silver halide contained in the photographic material represented by the curve 1 is 2 times the amount of that contained in the photographic material represented by the curve 2.

In the drawing, the curve 3 shows the case of photographic material containing the coupler according to the present invention which contains silver halide in an amount equal to that contained in the photographic material represented by the curve 2. As is clear from the drawing, the 2-equivalent coupler according to the present invention is sufficiently usable even when the amount of silver used is made one half the amount employed hitherto.

EXAMPLE 3

The exemplified yellow dye image-forming coupler (4) was dispersed in a mixed solvent comprising ethanol and water and then dissolved in a 10% caustic soda solution. The resulting solution was added to a gelatin solution containing 12% of gelatin and 5.13% of Alkanol B and then neutralized with acetic acid. Subsequently, the solution was dispersed in a silver iodobromide emulsion, which was then coated on a support and dried to prepare a light-sensitive color photographic material.

For comparison, a photographic material was prepared in the same manner as above, except that the coupler was replaced by a coupler identical in structure, except that it had a substituent-free active methylene group.

These photographic materials were individually exposed according to an ordinary procedure, developed with the same developer as in Example 1 and then treated in the same manner as in Example 1. The photographic properties of these photographic materials were as set forth in Table 2.

Table 2

| Coupler | Fog | Relative speed | $\lambda_{max}$ | $D_{max}$ |
|---|---|---|---|---|
| Exemplified coupler (4) | 0.12 | 225 | 450 | 2.65 |
| Control coupler | 0.10 | 100 | 450 | 1.85 |

As is clear from Table 2, the coupler according to the present invention gives excellent results even when Fisher's dispersion method is adopted.

EXAMPLE 4

A photographic emulsion containing the exemplified yellow dye image-forming coupler (3) was coated on a support to prepare a light-sensitive color photographic material, which was then treated with a weakly alkaline developer (pH 13) containing 2 g/l of $Na_2SO_3$ and 11 g/l of 4-N-ethyl-N-$\beta$-hydroxyethylaminoaniline. The resulting negative sheet was closely contacted at 24° C. for 3 minutes with an image-receiving sheet containing dimethyl-$\beta$-hydroxyethyl-$\gamma$-stearamidopropyl ammonium dihydrogen phosphate (mordant dye). Thereafter, the image-receiving sheet was peeled off and it was found that the yellow dye formed had been transferred to the image-receiving sheet to give an excellent positive image.

EXAMPLE 5

A light-sensitive photographic material containing an ordinary silver iodobromide emulsion was exposed and then subjected to ordinary external development by use of the aforesaid external developer incorporated with the exemplified yellow dye image-forming coupler (2).

For comparison, the same photographic material as above was exposed and then treated with an external developer incorporated with a coupler indentical in structure, except that it had a substituent-free active methylene group, which was used as a control.

The photographic properties of these photographic materials were as set forth in Table 3.

Table 3

| Coupler | Fog | Relative speed | $\lambda_{max}$ | $D_{max}$ |
|---|---|---|---|---|
| Coupler (2) | 0.05 | 220 | 442 | 2.68 |
| Control coupler | 0.04 | 100 | 443 | 2.46 |

What we claim is:

1. In a process for forming a yellow image in a silver halide light-sensitive color photographic material, comprising processing the photographic material by a color developer in the presence of an acyl acetanilide type 2-equivalent yellow coupler having active methylene herein and a split off group substituted for one of the two hydrogens on the active methylene, the improvement which comprises the split-off group being represented by the following general formula:

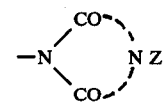

wherein Z is a group selected from alkylene, alkenylene, cycloalkylene, cycloalkenylene, terphenylene, arylene and pyridine-diyl.

2. A process of claim 1 wherein said coupler is selected from the group consisting of d-succinimido-$\alpha$-pivalyl-2-chloro-5-[$\gamma$-(2,3-di-t-amylphenoxy)-butylamide]acetanilide, $\alpha$-succinimido-$\alpha$-benzoyl-2-methoxyacetanilide, $\alpha$-(2-methoxysuccinimido)-$\alpha$-(p-dodecyloxybenzoyl)-3,5-dicarboxyacetanilide, $\alpha$-(cyclohexane-1,2-dicarboximido-$\alpha$-pivalylacetanilide, $\alpha$-(5-norbornene-2,3-dicarboximido)-$\alpha$-pivalylacetanilide, $\alpha$-phthalimido-$\alpha$-pivalyl-2-chloro-5-[$\gamma$-(2,4-di-t-amylphenoxy)butylamido]acetanilide, $\alpha$-phthalimido-$\alpha$-benzoyl-2-chloro-5-[$\gamma$-(2-4-di-t-amylphenoxy)-butylamido]acetanilide, $\alpha$-(4-nitrophthalimido)-$\alpha$-pivalylacetanilide, potassium-$\alpha$-(2,3-pyridinedicarboximido)-$\alpha$-furoyl-3,5-dicarboxyacetanilide, $\alpha$-maleimido-$\alpha$-pivalylacetanilide, $\alpha$-{3-[$\alpha$-(2,4-di-t-amylphenoxy)-butylamido]benzoyl}-$\alpha$-succinimido-2-methoxyacetanilide, $\alpha$-(2-methylsuccinimido)-$\alpha$-benzoyl-5-[$\alpha$-(n-dodecyloxycarbonyl)ethoxycarbonyl]-2-chloroacetanilide and $\alpha$-(2,2-dipropylmalonimido)-$\alpha$-pivalylacetanilide.

3. A process of claim 1 wherein said color developer comprising an aromatic primary amine developing agent.

4. A silver halide light-sensitive color photographic material comprising an acyl acetanilide type 2-equivalent yellow coupler having active methylene therein with a split off group substituted for one of the two hydrogens on the active methylene, said split-off group beinhg represented by the following general formula:

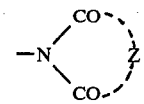

wherein Z is a group selected from alkylene, alkenylene, cycloalkylene, cycloalkenylene, terphenylene, arylene and pyridinediyl.

5. A method for forming dye images comprising processing an exposed silver halide photographic emulsion with an aqueous alkaline processing solution containing an aromatic primary amino developing agent in the presence of a yellow forming coupler having the following general formula

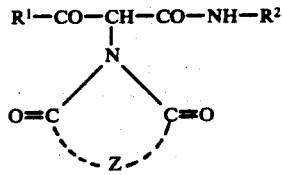

wherein $R^1$ is tertiary butyl; $R^2$ is an aryl group; and Z is selected from the group consisting of alkylene, alkenylene, cycloalkylene, cycloalkenylene, terphenylene, arylene and pyridine-diyl.

6. A method for forming dye images comprising processing an exposed silver halide photographic emulsion with an aqueous alkaline solution containing an aromatic primary amino developing agent in the presence of a yellow forming coupler having the general formula

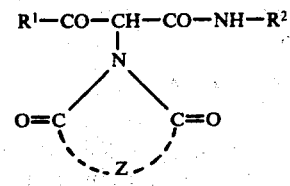

wherein $R^1$ is an aryl group; $R^2$ is an aryl group; and Z is selected from the group consisting of alkylene, alkenylene, cycloalkyllene, cycloalkenylene, terphenylene, arylene and pyridine-diyl.

* * * * *